(12) United States Patent
Lee et al.

(10) Patent No.: US 8,888,972 B2
(45) Date of Patent: Nov. 18, 2014

(54) ELECTROCHEMICAL BIOSENSOR STRUCTURE AND MEASURING METHOD USING THE SAME

(75) Inventors: Young Tae Lee, Gyeongsangbuk-do (KR); Seungro Lee, Daejeon (KR)

(73) Assignee: Center for Integrated Smart Sensors Foundation, Daejeon (KR)

( * ) Notice: Subject to any disclaimer, the term of this patent is extended or adjusted under 35 U.S.C. 154(b) by 676 days.

(21) Appl. No.: 13/124,500

(22) PCT Filed: May 18, 2009

(86) PCT No.: PCT/KR2009/002613
§ 371 (c)(1),
(2), (4) Date: Jul. 11, 2011

(87) PCT Pub. No.: WO2010/044525
PCT Pub. Date: Apr. 22, 2010

(65) Prior Publication Data
US 2011/0272295 A1 Nov. 10, 2011

(30) Foreign Application Priority Data
Oct. 16, 2008 (KR) .................. 10-2008-0101538

(51) Int. Cl.
G01N 27/327 (2006.01)
(52) U.S. Cl.
CPC .................. *G01N 27/3272* (2013.01)
USPC ................ 204/403.02; 204/403.04
(58) Field of Classification Search
CPC ........... G01N 27/3272; G01N 27/3274; C12Q 1/006; C12Q 1/54
See application file for complete search history.

(56) References Cited

U.S. PATENT DOCUMENTS

| | | | | |
|---|---|---|---|---|
| 6,299,757 | B1 * | 10/2001 | Feldman et al. | 205/775 |
| 6,767,441 | B1 * | 7/2004 | Cai et al. | 204/403.03 |
| 6,939,450 | B2 * | 9/2005 | Karinka et al. | 204/409 |
| 7,556,723 | B2 | 7/2009 | Funke et al. | |
| 2003/0042150 | A1 * | 3/2003 | Ryu et al. | 205/778 |
| 2004/0005721 | A1 | 1/2004 | Tanike et al. | |
| 2005/0016844 | A1 * | 1/2005 | Burke et al. | 204/403.01 |

FOREIGN PATENT DOCUMENTS

| | | |
|---|---|---|
| JP | 2008-527341 | 7/2008 |
| KR | 10-2007-0100362 | 10/2007 |
| KR | 10-2007-0121980 | 12/2007 |
| KR | 10-0854389 | 8/2008 |
| WO | WO 2004/113910 A1 * | 12/2004 ........... G01N 33/487 |

* cited by examiner

*Primary Examiner* — Alex Noguerola
(74) *Attorney, Agent, or Firm* — Dilworth & Barrese, LLP.

(57) ABSTRACT

The present invention provides there is provided an electrochemical biosensor electrode structure that includes: a working electrode and a reference electrode used as electrodes for sample measurement being arranged separately from each other in lengthwise direction of a sample insertion path, the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode; and at least two sample recognition electrodes used as electrodes for sample recognition being separated from each other and arranged adjacent and parallel to the working electrode and the reference electrode. The present invention minimizes the effect of the double layer capacitance and independently applies the sample recognition signal to accurately detect the sample insert time and velocity.

9 Claims, 8 Drawing Sheets

| Glucose concentration mmol/L(mg/dL) | Average(A) | Standard deviation(A) | Non-linear error(%) |
|---|---|---|---|
| $N = 100$ | $m = \frac{1}{n}\sum x_i$ | $\sigma^2 = \frac{1}{n}\sum(x_i - m)$ | $\frac{\text{Standard deviation}}{\text{Arithmetic average}} \times 100$ |
| 1.7 to 2.8(30 to 50) | 7.37E-06 | 1.09697E-07 | 1.49 |
| 2.9 to 6.1(51 to 100) | 1.03E-05 | 5.70455E-07 | 5.54 |
| 6.2 to 6.1(111 to 150) | 1.26E-05 | 4.39065E-07 | 3.48 |
| 8.4 to 13.9(151 to 250) | 1.69E-05 | 6.82113E-07 | 4.04 |
| 14 to 22.2(251 to 400) | 2.45E-05 | 4.48454E-07 | 1.83 |
| 22.3 to 33(401 to 594) | 3.25E-05 | 8.544E-07 | 2.63 |
|  |  |  | Total non-linear error = 3.17 |

ELECTROCHEMICAL BIOSENSOR STRUCTURE AND MEASURING METHOD USING THE SAME

TECHNICAL FIELD

The present invention relates to an electrochemical biosensor structure and a measurement method using the same, and more particularly, to an electrochemical biosensor electrode structure and a measurement method using the same that minimizes double layer capacitance and thereby can realize rapid and accurate measurements of response signals to a bio sample.

BACKGROUND ART

It is chemically and clinically important to do qualitative and quantitative analyses of materials contained in a bio sample, including, for example, blood glucose for diabetic patients or cholesterol in blood that is a factor of many adult diseases.

As known in the art, measuring enzymatic activity for a specific material contained in a bio sample (hereinafter, referred to as "sample") more rapidly with good reproducibility is very important to the electrochemical biosensor using enzymatic activity such as, for example, glucose sensor, uric acid sensor, protein sensor, DNA sensor or sucrose sensor for clinical chemical tests, or GOT (Glutamate-Oxaloacetate Transaminase) or GPT (Glutamate-Pyruvate Transaminase) sensor for liver function test.

The biosensor is composed of an identification part for identifying an analyte target, and a conversion part that is in charge of conversion to electrical signals. Biomaterials are used as the identification part of the biosensor. The biomaterial recognizes an analyte target to cause a chemical or physical change, and the conversion part converts the chemical or physical change to electrical signals. The identification part and the conversion part are collectively called "biosensor electrode".

Generally, the measurement method using the conventional strip type biosensor involves inserting a sample into a sample insertion path by way of capillary action, which is stronger than terrestrial gravity and acquired through plasma or chemical surfactant treatment in the course of fabrication, accumulating the sample in the sample insertion path and then doing a qualitative and quantitative analysis of the sample.

The measurement method normally further includes, prior to the sample measurement, detecting a sample insert timing that is when the inserted sample begins to accumulate in the sample insertion path.

Conventionally, a sample insertion detection signal is applied to a working electrode and a reference electrode of the biosensor to detect the sample insert timing and, after an elapse of predetermined time, a sample measurement signal is applied to the working electrode and the reference electrode to measure the sample. In other words, the sample insert timing is determined by calculating the time taken to make the sample completely inserted into the sample insertion path in all volume from the arrival time of the sample at the working electrode and the reference electrode. Then, a predetermined time later, the sample measurement signal is applied to the working electrode and the reference electrode to take a measurement of the sample.

This case encounters a problem that the sample insertion detection signal applied to detect the sample insert timing is too early reactive to the sample on the surface of the working electrode and the reference electrode, which are important as electrodes for measurement, to form an electric double layer (EDL). The electric double layer, which usually appears on the interface between adjacent different substances (electrode, sample, or solution), is formed when electric field is applied to the interface. The capacitance of the electric double layer, which is called "double layer capacitance (DLC)", is of a meager amount but can be included in the current signal measured when the sample detection signal is applied. This causes a distortion of the measurement signal of the biosensor and affects the measurement results.

The viscosity of the sample depends on the type of the sample and, if not significant, may determine the sample's accumulating velocity or time in the sample insertion path. This may also affect the measurement results because the measurement begins after an elapse of predetermined time that is calculated as the time taken to accumulate the sample completely into the path from the sample insert timing. It is therefore considerably problematic in regard to accuracy of measurement to determine the timing to apply the sample measurement signal by control of timing.

DISCLOSURE OF INVENTION

Technical Problem

It is therefore an object of the present invention to provide a biosensor electrode structure and a measurement method using a biosensor that solves the problems with the prior art.

It is another object of the present invention to provide a biosensor electrode structure and a measurement method using a biosensor that effectively eliminates double layer capacitance and enables accurate detection of response signals without distortion from a working electrode and a reference signal, which are electrodes for measurement.

It is still another object of the present invention to provide a biosensor electrode structure and a measurement method using a biosensor that can control the sample insert velocity, which depends on the type of the sample.

Technical Solution

To achieve the objects of the present invention, there is provided an electrochemical biosensor electrode structure that includes: a working electrode and a reference electrode used as electrodes for sample measurement being arranged separately from each other in lengthwise direction of a sample insertion path, the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode; and at least two sample recognition electrodes used as electrodes for sample recognition being separated from each other and arranged adjacent and parallel to the working electrode and the reference electrode.

The at least two sample recognition electrodes are arranged between the working electrode and the reference electrode. The ends of the at least two sample recognition electrodes are adjacent to the end of the sample insertion path.

The at least two sample recognition electrodes recognize a sample in response to a sample recognition signal. The sample recognition signal is applied independent of a sample measurement signal applied to the reference electrode or the working electrode to recognize the sample.

The electrochemical biosensor electrode structure further includes a strip recognition electrode for sensing the moment that a biosensor having the biosensor electrode is inserted into a measurement device to take a measurement.

The working electrode and the reference electrode are separated from each other at a separation distance of 50 to 120 µm in a portion thereof corresponding to the sample insertion path.

In accordance with another embodiment of the present invention, there is provided a structure for electrochemical biosensor that includes: a bottom plate including electrodes for sample measurement, and at least two sample recognition electrodes arranged separately from the electrodes for sample measurement on an insulating substrate, the electrodes for sample measurement including a working electrode and a reference electrode, the working electrode and the reference electrode being arranged separately from each other in lengthwise direction of a sample insertion path, the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode, the at least two sample recognition electrodes being separated from each other and arranged adjacent and parallel to the working electrode and the reference electrode; a middle plate having a double-coated adhesive insulating film structure with the sample insertion path formed thereon; and a top plate having at least two air exhaust holes being formed on the insulating substrate in correspondence to the end of the sample insertion path. The at least two air exhaust holes being provided correspondingly to the ends of the at least two sample recognition electrodes to vertically overlap the ends of the at least two sample recognition electrodes.

The at least two sample recognition electrodes recognize a sample in response to a sample recognition signal. The sample recognition signal is applied independent of a sample measurement signal applied to the reference electrode or the working electrode to recognize of the sample.

A first sample recognition electrode as the one of the at least two sample recognition electrodes is provided for applying a sample recognition signal, and a second sample recognition electrode as the other one of the at least two sample recognition electrodes is provided for receiving a sample arrival signal.

The working electrode and the reference electrode are separated from each other at a separation distance of 50 to 120 µm in a portion thereof corresponding to the sample insertion path.

In accordance with still another embodiment of the present invention, where is provided a sample measurement method using a biosensor that includes: (a) preparing the biosensor having electrodes for sample measurement, and at least two sample recognition electrodes provided separately from the electrodes for sample measurement, the electrodes for sample measurement including a working electrode and a reference electrode, the at least two sample recognition electrodes receiving a sample recognition signal controlled separately from a sample measurement signal applied to the working electrode and the reference electrode; (b) applying the sample recognition signal to the one of the at least two sample recognition electrodes to determine whether a sample has arrived or not, the sample recognition signal being generated and controlled independent of the sample measurement signal; and (c) if the sample has arrived, applying the sample measurement signal to the working electrode and the reference electrode and measuring a response signal to the sample.

In the step (b), whether the sample has arrived is determined by receiving a sample arrival signal through the other one of the at least two sample recognition electrodes.

The working electrode and the reference electrode are arranged separately from each other in lengthwise direction of a sample insertion path. Each of the working electrode and the reference electrode has at least one projection and at least one recess alternately arranged on a portion thereof corresponding to the sample insertion path. The projection of the working electrode is correspondingly adjacent to the recess of the reference electrode, and the recess of the working electrode is correspondingly adjacent to the projection of the reference electrode.

In accordance with further another embodiment of the present invention, there is provided a method for fabricating an electrochemical biosensor electrode that includes: forming a first conductive thin film adhesively on an insulating substrate by lamination; coating a photosensitivity dry film on the first conductive thin film by lamination, and performing a photo and etching process to form an electrode pattern comprising a material of the first conductive thin film, the electrode pattern integrally having at least two sample recognition electrodes and electrodes for sample measurement, the electrodes for sample measurement including a working electrode and a reference electrode, the working electrode and the reference electrode being arranged separately from each other in lengthwise direction of a sample insertion path, the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode; and forming a second conductive thin film on the surface of the electrode pattern, the second conductive thin film having a higher conductivity than the electrode pattern.

The insulating substrate is a polymer film comprising at least one material selected from polyester, polycarbonate, polystyrene, polyimide, polyvinylchloride, polyethylene, or polyethyleneterephthalate(PET).

The first conductive thin film includes a material of copper or copper alloy.

The method further includes: forming a nickel or chrome layer between the first and second conductive thin films by plating to enhance adhesion strength between the first and second conductive thin films.

The second conductive thin film is formed through gold or platinum plating.

The at least two sample recognition electrodes include two sample recognition electrodes adjacent to the working electrode or the reference electrode.

The working electrode and the reference electrode are separated from each other at a separation distance of 50 to 120 µm in a portion thereof corresponding to the sample insertion path.

The insulating substrate with the working electrode, the reference electrode and the at least two sample recognition electrodes formed thereon is a bottom plate of the biosensor comprising top, middle and bottom plates. The method further includes: after preparation of the bottom plate of the biosensor, forming the middle plate of a double-coated adhesive insulating film structure with the sample insertion path formed thereon; and forming the top plate having at least two air exhaust holes corresponding to the end of the sample insertion path in the insulating substrate. The at least two air exhaust holes are provided correspondingly to the ends of the at least two sample recognition electrodes to vertically overlap the ends of the at least two sample recognition electrodes.

Advantageous Effects

The present invention minimizes the effect of the double layer capacitance, independently applies the sample recognition signal, and accurately detects the sample insert time and velocity irrespective of the viscosity of the sample to be measured. Additionally, the present invention has no problem in regard to a distortion of the measurement signal in taking a measurement of the sample, so the sample measurement can be accomplished more rapidly with high reproducibility.

MODE FOR THE INVENTION

Hereinafter, the preferred embodiments of the present invention will be described in detail with reference to the accompanying drawings, which are intended for purpose of illustration only and are not intended to limit the scope of the invention.

Figure 1:
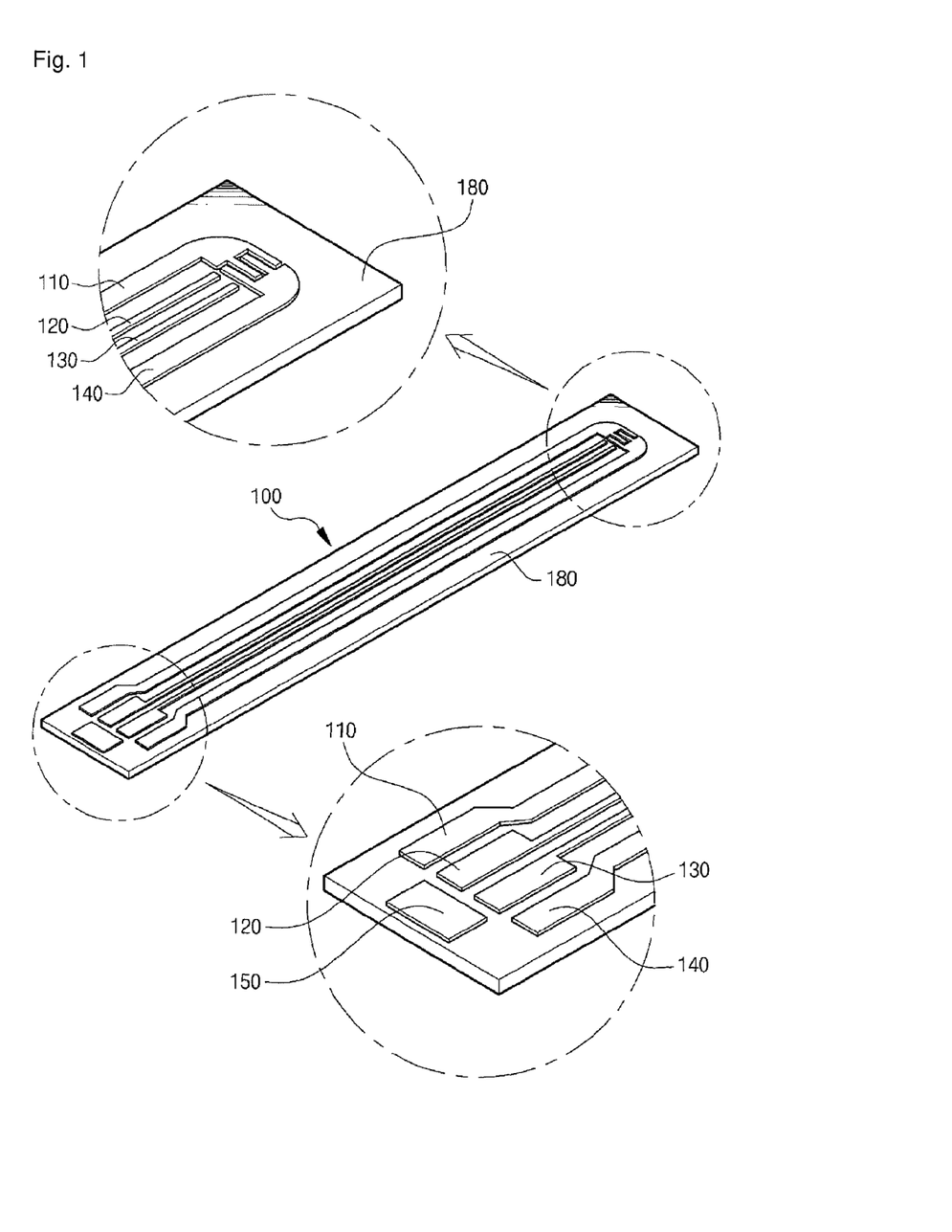
FIG. 1 shows an electrochemical biosensor electrode structure according to an embodiment of the present invention.

FIG. 1 shows an electrochemical biosensor electrode structure according to an embodiment of the present invention.

As illustrated in FIG. 1, biosensor electrodes 110, 120, 130 and 140 according to an embodiment of the present invention are fabricated on an insulating substrate 100. The method for fabricating the biosensor electrodes 110, 120, 130 and 140 is illustrated in FIGS. 8 to 14.

The biosensor electrodes 110, 120, 130 and 140 include a working electrode 110 and a reference electrode 140 used as electrodes for sample measurement, and at least two sample recognition electrodes 120 and 130 used as electrodes for sample recognition.

Generally, two electrodes are used in measuring the electric potential difference between two points in order to determine electrode potential in an electrolyte solution. The electrode where the electric potential is measured is called "working electrode", and the other electrode connected to measure the electric potential difference is called "reference electrode".

Though the electrodes are expediently differentiated into working electrode 110 and reference electrode 140 as chosen in terms of definition in the description, it is apparent to those skilled in the art that the working electrode 110 can be used as the reference electrode 140, and vice versa.

The working electrode 110 and the reference electrode 140 are separated from each other and arranged in lengthwise direction of a sample insertion path (as denoted by 210 in FIG. 2) into which a sample is inserted.

The portion corresponding to the sample insertion path 210 is enlarged in the upper part of FIG. 1. Referring to the enlarged view, each of the working electrode 110 and the reference electrode 140 has at least one projection and at least one recess that are alternately arranged on a portion corresponding to the sample insertion path 210 (for example, the portion where the sample insertion path forms).

The projection of the working electrode 110 is arranged correspondingly adjacent to the recess of the reference electrode 140, and the recess of the working electrode 110 is arranged correspondingly adjacent to the projection of the reference electrode 140. In other words, the projection of the working electrode 110 is provided to fit into the recess of the reference electrode 140, and the projection of the reference electrode 140 is provided to fit into the recess of the working electrode 110. When in engagement, the working electrode 110 is not in direct contact with the reference electrode 140 but separated from the reference electrode 140 at a predetermined distance. The separation distance between the working electrode 110 and the reference electrode 140 ranges from 50 to 120 μm in the portion corresponding to the sample insertion path 210.

A sample measurement signal may be applied when the working electrode 110 and the reference electrode 140 are in use for measurement.

Electrode arrangement and structure plays an important role in the related chemical reactions, because oxidation-reduction reactions that are crucial to the electrochemical measurement occur through electron transfer between the electrode interface and the solution. Accordingly, the working electrode 110 and the reference electrode 140 are alternately arranged in a specified portion as described above, so the response signal between the electrodes is effectively detected.

The working electrode 110 and the reference electrode 140 are formed as illustrated in the fabrication method of FIGS. 8 to 14, which involves laminating a conductive thin film on an insulating film and patterning biosensor electrodes through photolithography. The separation distance between the electrodes is 50 μm at minimum as currently available by the wet etching technology, and may be reduced to less than 50 μm according to other advanced technologies.

Additionally, the amount of the sample needed for electrochemical measurement is minimized to less than 0.25 μl, and a proper distance between the alternately arranged electrodes provided is about 80 μm. The separation distance between the working electrode 110 and the reference electrode 140 is readily available in the range of 50 to 120 μm.

As the working electrode 110 and the reference electrode 140 are arranged with such a minute separation distance to each other in a specified portion, it takes a short time to reach a rectified-state current value, resulting in a fast response time. And, such a small area involves a low capacitance and hence a low noise signal in comparison to the faraday current, and the current having such a small absolute value causes a low voltage drop from the solution resistance. The current with a small absolute value, on the other hand, requires the use of a low-noise amplifier having a high magnification, which amplifier can be readily available according to the conventional technologies.

More advantageously, enzyme immobilization, which is one of the crucial steps in the biosensor fabrication, can be achieved through physically and structurally uniform dispersion of enzyme between the electrodes.

In an attempt to increase the analytical sensitivity, an embodiment of the present invention uses a plurality of microelectrodes arranged with a predetermined separation distance wide enough to avoid the overlap of diffusion layer, so the signal itself can be amplified to make the present invention used as a remarkably advantageous amperometric sensor.

Between the working electrode 110 and the reference electrode 140 are arranged at least two sample recognition electrodes 120 and 130. For expediency in the description, the at least two sample recognition electrodes 120 and 130 include two sample recognition electrode 120 and 130. It is however apparent to those skilled in the art that the present invention may include three or more sample recognition electrodes.

The sample recognition electrodes 120 and 130 are provided between the working electrode 110 and the reference electrode 140, while none of the sample recognition electrodes 120 and 130 is formed in the portion where the working electrode 110 and the reference electrode 140 are provided in an alternating arrangement. In other words, the sample recognition electrodes 120 and 130 are not formed in the portion where the sample insertion path 210 is formed, except for a portion corresponding to the end of the sample insertion path 210. Accordingly, the ends of the sample recognition electrodes 120 and 130 are adjacent to the end of the sample insertion path 210. This arrangement structure is necessary to recognize the sample.

The sample recognition electrodes 120 and 130 are adjacent and parallel to the working electrode 110 or the reference electrode 140. Provided with the working electrode 110, for example, the first sample recognition electrode 120 is formed adjacent to the working electrode 110, the second sample recognition electrode 130 adjacent to the first sample recognition electrode 120, and finally the reference electrode 140 adjacent to the second sample recognition electrode 130. The one (for example, sample recognition electrode 120) of the sample recognition electrodes 120 and 130 may be an electrode for receiving a sample recognition signal in taking a measurement of the sample, and the other (for example, sample recognition electrode 130) may be an electrode for receiving a sample arrival signal.

The sample recognition electrodes 120 and 130 are arranged in a minimum area at the end of the sample insertion path 210, apart from the working electrode 110 and the reference electrode 140. As will be described later, two air exhaust holes 310 and 320 are provided vertically above the sample recognition electrodes 120 and 130 in correspondence to the sample recognition electrodes 120 and 130. According to this structure, the sample arrival signal can be acquired only when the sample is completely inserted into the sample insertion path 210, while the sample recognition electrodes 120 and 130 are not affected by the viscosity of the sample, surrounding environments (e.g., temperature, humidity, etc.), or the like.

Any other signal is not applied to the working electrode 110 and the reference electrode that are important for measurement, when the sample arrival signal is acquired.

The end portion of sample recognition electrodes 120 and 130 are separated from the working electrode 110 and the reference electrode 140 and arranged in a minimum area at the end of the sample insertion path 210.

So this structure is designed to prevent the working electrode 110 and the reference electrode 140 from being affected by the double layer capacitance that occurs when the sample is recognized.

In the subsequent sample measurement, a separate measurement signal independent of the sample recognition signal is applied only to the working electrode 110 and the reference electrode 140 that are independently arranged, to take a measurement.

The working electrode 110, the reference electrode 140, and the sample recognition electrodes 120 and 130, except for the portion corresponding to the sample insertion path 210, are arranged in a predetermined width and separated from one another in a parallel arrangement. The width of the working electrode 110 or the reference electrode 140 is greater than that of the sample recognition electrode 120 or 130. This is for achieving more stable measurement with better reproducibility by reducing the resistance of the working electrode 110 and the reference electrode 140 lower than the resistance of the sample recognition electrodes 120 and 130 and thereby minimizing the effect of noise on the detected signal during sample measurement.

The lead terminal portion (referring to the lower enlarged view in FIG. 1), where an external signal or a response signal to the external signal is applied to the working electrode 110, the reference electrode 140 and the sample recognition electrodes 120 and 130, may have a width greater than the normal width of the working electrode 110, the reference electrode 140 and the sample recognition electrodes 120 and 130. This is to facilitate the signal transfer.

The biosensor electrodes may further include a strip recognition electrode 150 in addition to the working electrode 110, the reference electrode 140 and the sample recognition electrodes 120 and 130. The strip recognition electrode 150 is provided on the assumption that the biosensor is formed in the test strip type. For biosensors of a type other than test strips, the strip recognition electrode 150 is not provided, or electrodes of another type are used.

The strip recognition electrode 150 generates a strip insertion signal by sensing the test strip at the moment the test strip type biosensor including biosensor electrodes is inserted into the body of a measurement device. Accordingly, the strip recognition electrode 150 may be arranged ahead of the portion where the lead terminals of the individual electrodes are arranged, which is most ahead of the part of the biosensor inserted into the measurement device.

The body of the measurement device, if not illustrated, is a device into which the biosensor is inserted to measure the sample, which is well known to those skilled in the art.

Figure 2:
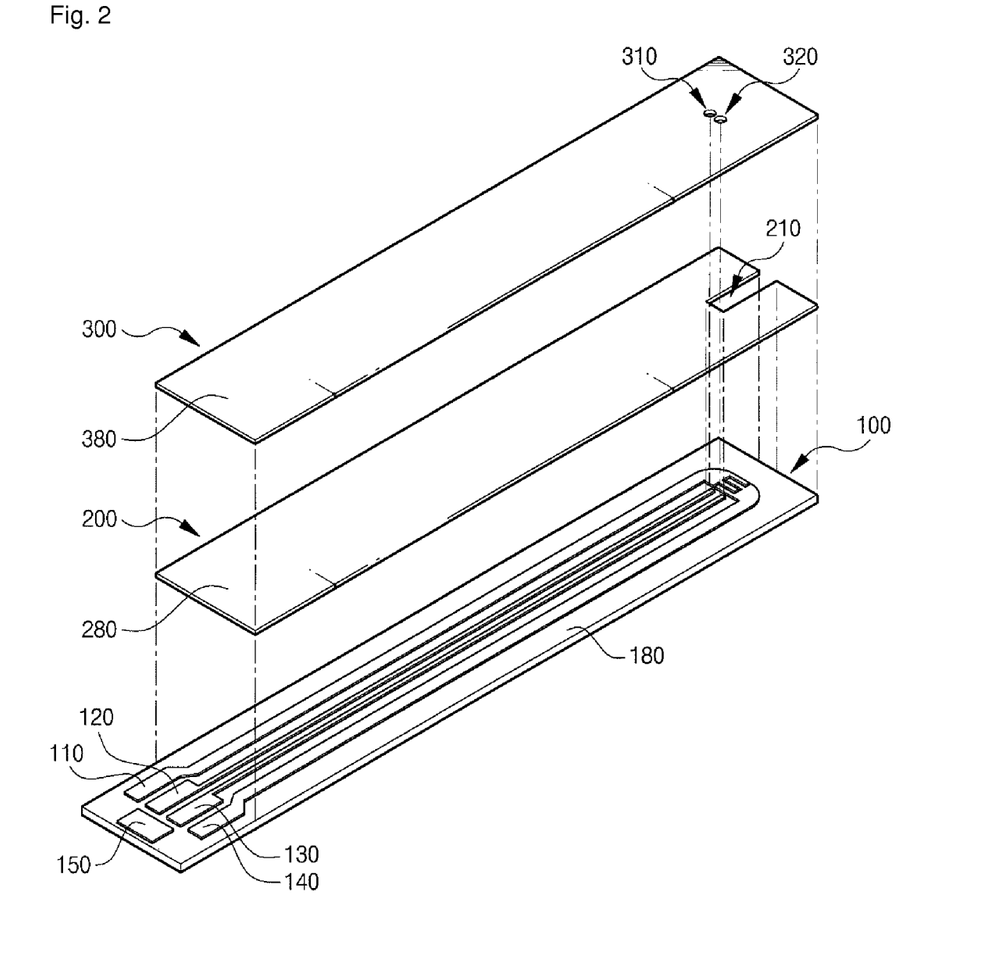
FIGS. 2 to 5 are diagrams for explaining a test strip type biosensor structure having the electrode structure of FIG. 1.
Figure 3:
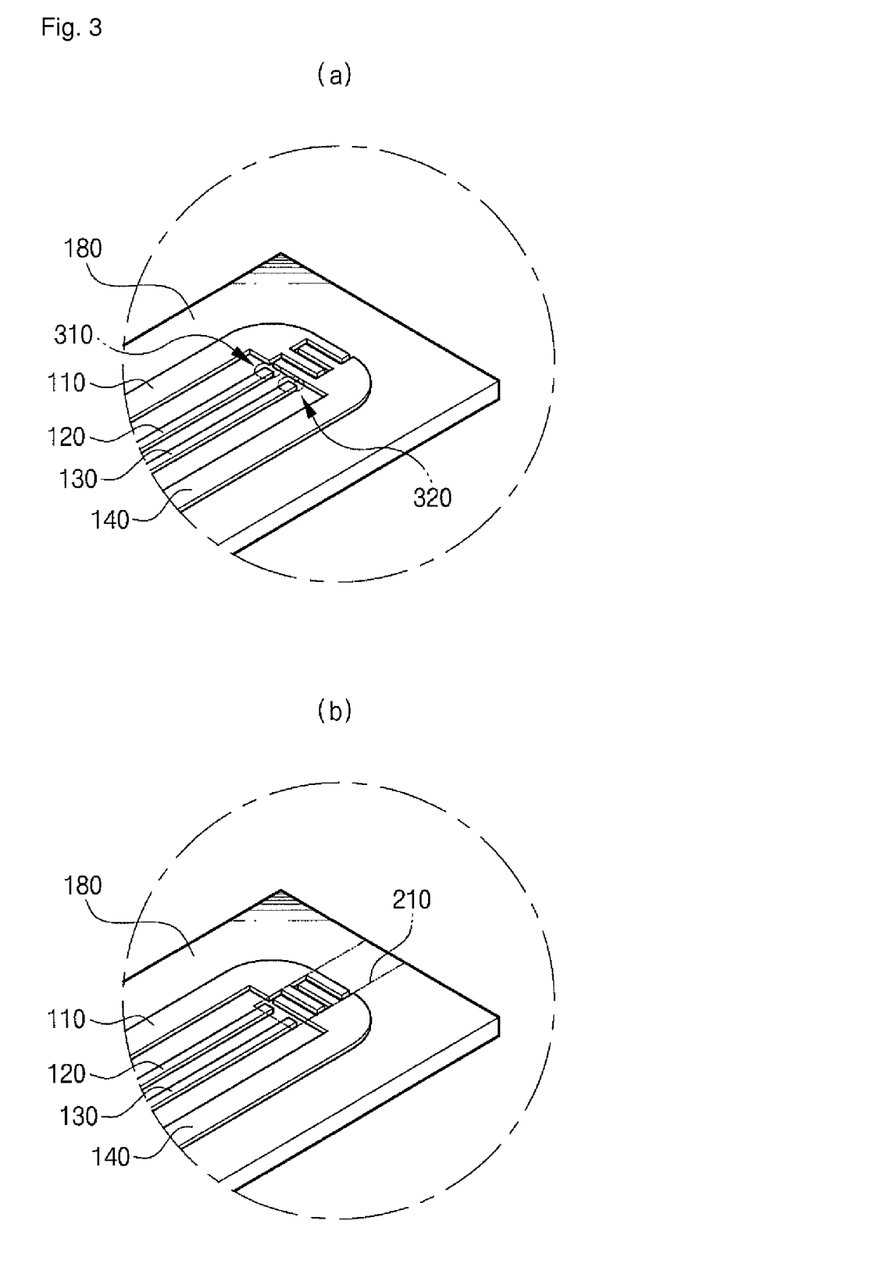
Figure 4:
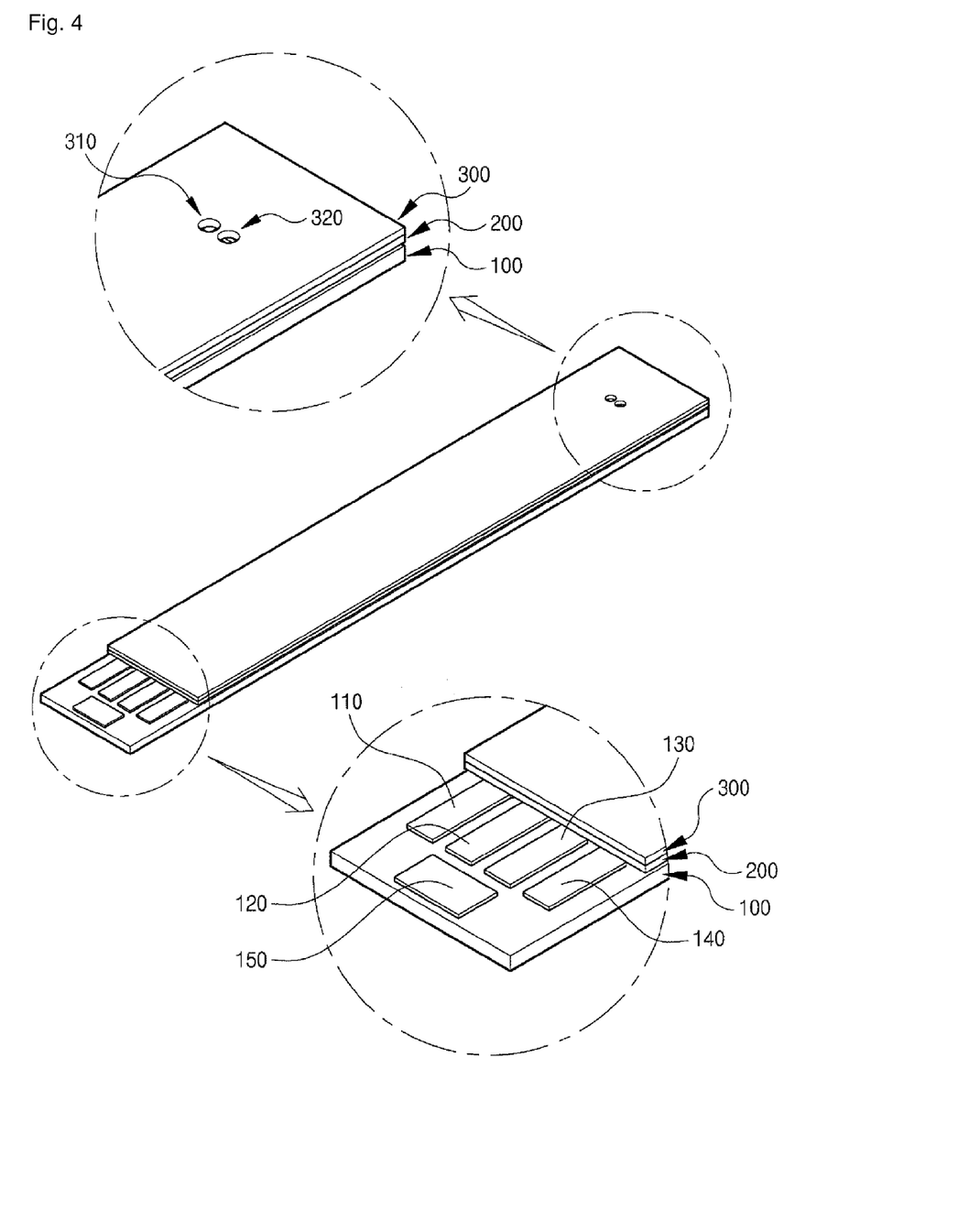
Figure 5:
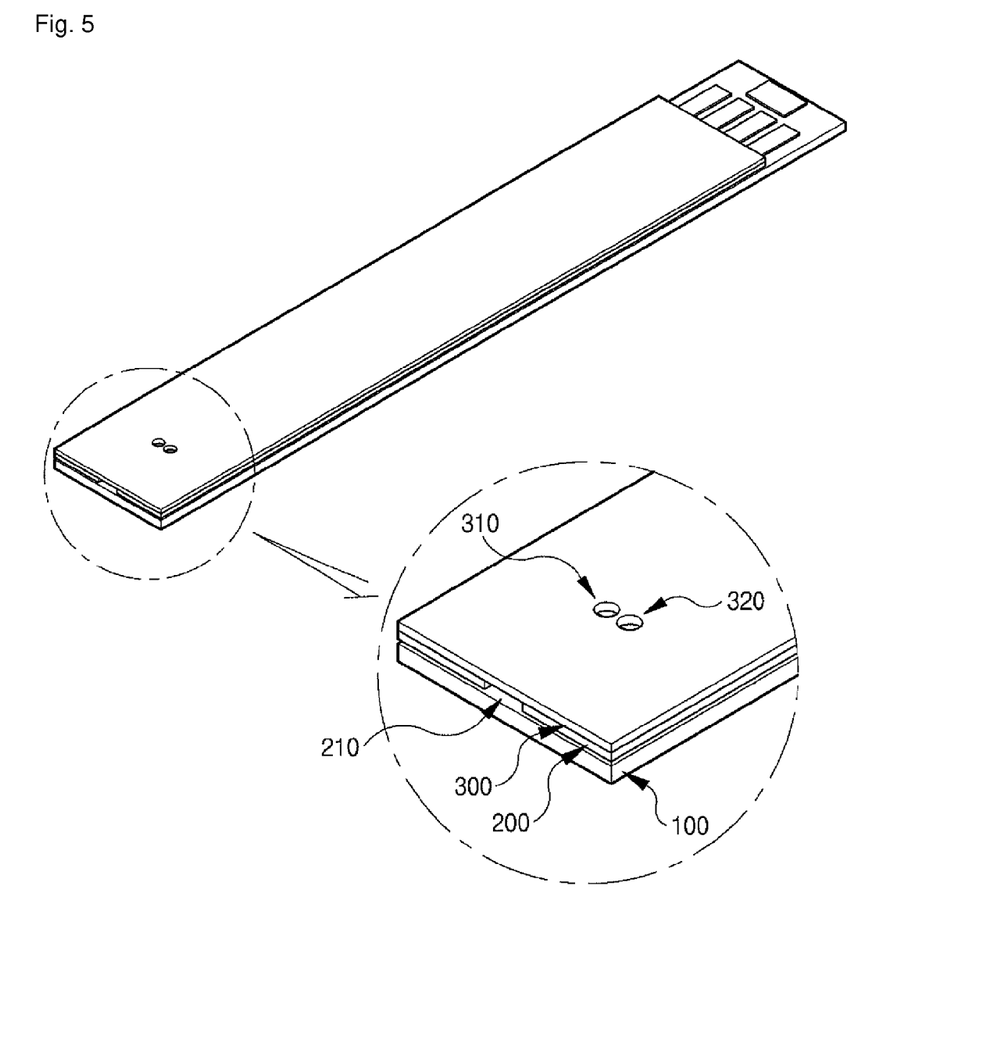

FIGS. 2 to 5 are diagrams for explaining a test strip type biosensor structure having the electrode structure of FIG. 1: FIG. 2 is an exploded perspective of the biosensor; FIG. 3 is an enlarged view showing the corresponding and positional relationship of the individual component parts in the exploded perspective of FIG. 2; FIG. 4 is an assembled perspective of the biosensor; and FIG. 5 is an enlarged view showing the air exhaust holes and the sample insertion path in detail.

As illustrated in FIG. 2, the electrochemical biosensor according to another embodiment of the present invention has an assembled structure of a test strip bottom plate 100, a test strip middle plate 200, and a test strip top plate 300.

The test strip bottom plate 100 includes biosensor electrodes 110, 120, 130, 140 and 150 provided on an insulating substrate 180, where the biosensor electrodes 110, 120, 130, 140 and 150 is arranged as illustrated in FIG. 1.

The test strip middle plate 200 includes the sample insertion path 210 formed on a double-coated adhesive insulating film 280. The sample insertion path 210 has a recess in a predetermined depth on the lateral side of the double-coated adhesive insulating film 280.

The sample insertion path 210 of this recess structure, as can be seen in the enlarged view of FIG. 3(b), corresponds to the portion where projections and recesses are alternately arranged on the working electrode 110 and the reference electrode 140 provided on the test strip bottom plate 100. The end of the sample insertion path 210 extends to the ends of the at least two sample recognition electrodes 120 and 130. In FIG. 3(b), the sample insertion path 210 is indicated by a dotted line.

With the test strip bottom plate 100 adhesively assembled with the test strip middle plate 200, the sample insertion path 210 exposes the portion where projections and recesses are alternately arranged on the working electrode 110 and the reference electrode 140, and the ends of the at least two sample recognition electrodes 120 and 130.

The test strip top plate 300 includes at least two air exhaust holes 310 and 320 formed in correspondence to the end of the sample insertion path 210 on the insulating substrate 380. The at least two air exhaust holes 310 and 320 are provided correspondingly to the at least two sample recognition electrodes 120 and 130 to vertically overlap the ends of the at least two sample recognition electrodes 120 and 130.

Accordingly, when the test strip bottom plate 100, the test strip middle plate 200 and the test strip top plate 300 are adhesively assembled together, as illustrated in the enlarged views of FIGS. 3(a) and 3(b), the end of the sample insertion path 210 and the ends of the at least two sample recognition electrodes 120 and 130 are exposed. The term "exposed" as used herein means that the end of the sample insertion path 210 and the ends of the at least two sample recognition electrodes 120 and 130 can be seen through the air exhaust holes 310 and 320.

The end of the sample insertion path 210 as described in the present invention is the final point at which the sample put into the sample insertion path 210 arrives. The ends of the sample recognition electrodes 120 and 130 are the portions corresponding to the final arrival point of the sample.

Each of the at least two air exhaust holes 310 and 320 is formed in a minimum area at a position corresponding to the lengthwise end of the sample insertion path 210 and the ends of the at least two sample recognition electrodes 120 and 130. Here, the number of the at least two air exhaust holes 310 and 320 is determined correspondingly to the number of the at least two sample recognition electrodes 120 and 130. For example, at least three air exhaust holes 310 and 320 are provided for at least three sample recognition electrodes 120 and 130.

The at least two air exhaust holes 310 and 320 are designed in consideration of the property that the sample moves along the inclined plane of the sample insertion path 210 by way of surface activity when it passes through the sample insertion path 210 by capillary action. Namely, the at least two air exhaust holes 310 and 320 are configured for the purpose of effectively collecting the sample from the sample insertion path 210 at the position of the portion where projections and recesses are alternately arranged on the working electrode 110 and the reference electrode 140.

With two sample recognition electrodes 120 and 130 and two air exhaust holes 310 and 320, the two air exhaust holes 310 and 320 are arranged as illustrated in the partial enlarged view of FIG. 3(a), where the ends of the sample recognition electrodes 120 and 130 are accurately positioned in a portion vertically below (vertically overlapping) the air exhaust holes 310 and 320. To be more precise, the first air exhaust hole 310 of the two air exhaust holes 310 and 320 vertically overlaps the end of the first sample recognition electrode 120 of the two sample recognition electrodes 120 and 130, while the second air exhaust hole 320 vertically overlaps the end of the second sample recognition electrode 130.

With the test strip bottom plate 100, the test strip middle plate 200 and the test strip top plate 300 assembled together, part of the electrodes of the test strip bottom plate 100 is exposed, as illustrated in FIG. 4.

Viewed in the lengthwise direction of the sample insertion path 210, the test strip middle plate 200 and the test strip top plate 300 are shorter than the test strip bottom plate 100. Accordingly, the assembly of the test strip bottom plate 100, the test strip middle plate 200 and the test strip top plate 300 exposes the portion where the electrodes 110, 120, 130 and 140 of the test strip bottom plate 100 applies or receives signals. The whole of the strip recognition electrode 150 is also exposed.

As illustrated in FIG. 5, the sample insertion path 210 has a recess or groove structure in the assembly structure that includes the test strip middle plate 200 on the test strip bottom plate 100, and the test strip top plate 300 on the test strip middle plate 200.

Figure 6:
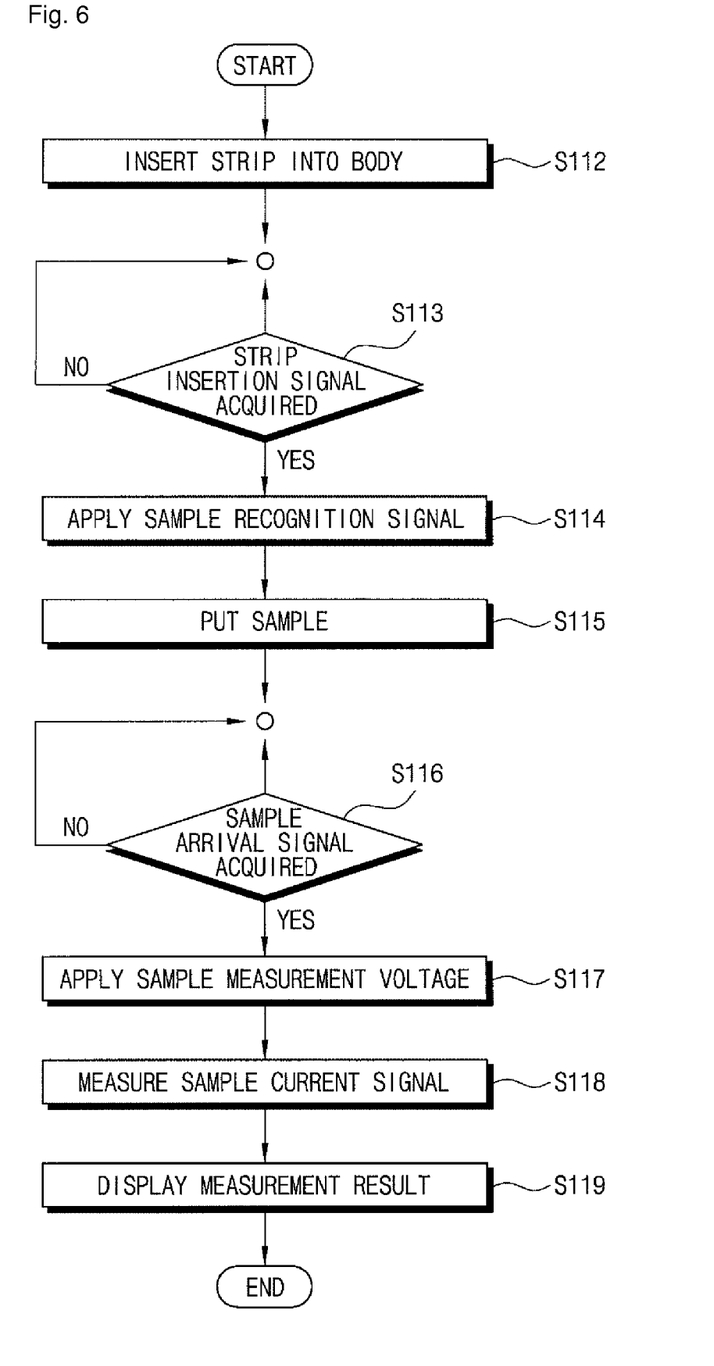
FIG. 6 is a flowchart showing the measurement procedure using the biosensor of FIGS. 2 to 5.

FIG. 6 is a flowchart showing the measurement procedure using the biosensor of FIGS. 2 to 5. As described above, a measurement device is separately provided for taking a measurement of the sample.

As illustrated in FIG. 6, the biosensor of FIGS. 2 to 5 is inserted into the body of the measurement device provided to take a measurement (S112). The strip recognition electrode 150 recognizes insertion of the biosensor and generates a strip insertion signal. The measurement device acquires (receives) the strip insertion signal (S113). If not acquiring the strip insertion signal from the measurement device (NO), the strip recognition electrode 150 awaits until the strip insertion signal is acquired.

After acquisition of the strip insertion signal from the measurement device (YES), a sample recognition signal to recognize the sample is applied to the first sample recognition electrode 120 (S114). It is expediently described that the sample recognition signal is applied to the first sample recognition electrode 120, although it can also be applied to the second sample recognition electrode 130.

The sample is inserted through the sample insertion path 210 (S115). It is then determined whether or not the sample has arrived. That is, a sample arrival signal is generated, and the acquisition (reception) of the sample arrival signal is determined (S116). The sample arrival signal is generated only when the sample arrives accurately at the first and second air exhaust holes 310 and 320 from the sample insert point. The sample arrival is determined by whether the sample has arrived at the air exhaust holes 310 and 320.

The sample arrival signal is acquired through the second sample recognition electrode 130. If applied to the second sample recognition electrode 130 rather than to the first sample recognition electrode 120, the sample arrival signal is acquired through the first sample recognition electrode 120.

If the sample does not arrive at the air exhaust holes 310 and 320 (NO), the sample arrival signal is not generated. And a sample measurement signal to measure the sample is not applied, either. If the sample arrives at the air exhaust holes 310 and 320 and the sample arrival signal is acquired (YES), the measurement device applies the sample measurement signal for sample measurement to the working electrode 110 and the reference electrode 140 (S117).

The sample measurement signal is independent of the sample recognition signal in regard to generation and control. It is one thing to generate and control the sample measurement signal, and it is another to generate and control the sample recognition signal.

Characteristic to the biosensor of the present invention, the sample recognition signal is applied only to the sample recognition electrodes 120 and 130 rather than to the working electrode 110 or the reference electrode 140. The sample measurement signal is not applied to the sample recognition electrodes 120 and 130 but to the working electrode 110 and the reference electrode 140.

In the electrochemical sample measurement, for example, the applied sample measurement signal is positive(+) to the working electrode 110 and negative(−) to the reference electrode 140.

After the sample measurement signal is applied, a sample current signal is acquired (received) through the working electrode 110 and the reference electrode 140 and then measured (S118). The measurement result is then displayed (S119). The sample current signal is measured between the working electrode 110 and the reference electrode 140, and the current is quantitatized to calculate the concentration of the sample, which is given in mM or mg/dL.

In the present invention, as described above, the sample recognition electrodes 120 and 130 are independent of the reference electrode 140 and the working electrode 110 that are electrodes for sample measurement, in the aspect of structure or signal applying method. Even for different types of samples (for example, in regard to viscosity, etc.), the present invention can take a measurement at an accurate timing (sample arrival point) without being affected on the sample insert time or velocity.

Particularly, the sample measurement signal controlled independent of the sample recognition signal is applied only to the working electrode 110 and the reference electrode 140. This has a considerably significant meaning in determining the timing to apply the sample measurement signal that is crucial in the electrochemistry. Accordingly, the present invention realizes an effective control of the sample insert time and velocity that may depend on the type of the sample, and rapid and accurate measurements of the sample.

More advantageously, the present invention separately provides and controls the sample recognition electrodes 120 and 130 independent of the working electrode 110 and the reference electrode 140 used as electrodes for sample measurement, so a rapid and accurate measurement can be achieved without a need of considering the generation of distorted signals from double layer capacitance or the effect of inaccurate insertion of the sample.

Figure 7:
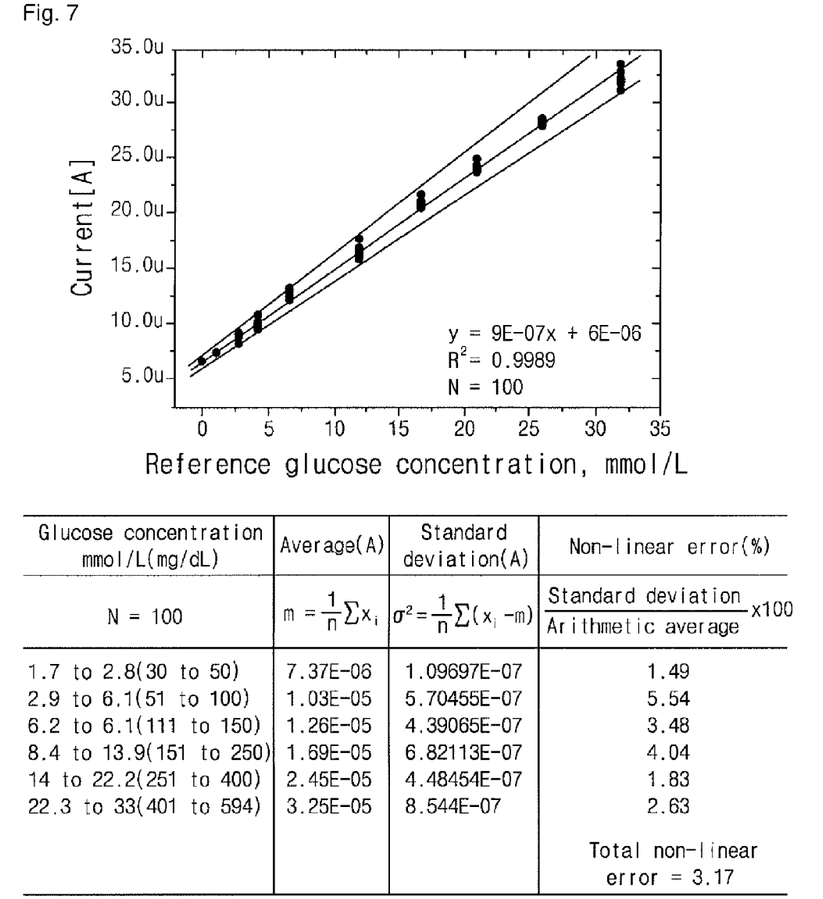
FIG. 7 is a graph and table showing the measurement results of FIG. 6.

FIG. 7 is a graph and table showing the results of the measurement method of FIG. 6. More specifically, FIG. 7 presents exemplary measurement results of a glucose sensor using a biosensor having an extremely low electric resistance (less than 0.1Ω) on an insulating substrate, and a measurement method using the biosensor.

As shown in the graph and table of FIG. 7, which shows the reproducibility of a measurement current signal for a glucose concentration (Buffer~33 mM), the measurement is carried out 100 times and considerably accurate to give a non-linear error of less than 3.17% within 3 seconds.

FIGS. 8 to 14 are cross-sections showing a procedure for fabricating the biosensor electrode of FIG. 1.

Figure 8:
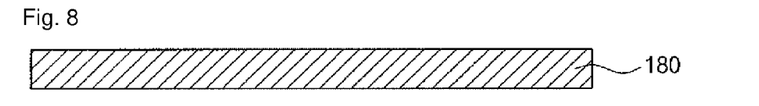
FIGS. 8 to 14 are cross-sections showing a procedure for fabricating the biosensor electrode of FIG. 1.

As illustrated in FIG. 8, an insulating substrate 180 is prepared. The insulating substrate 180 may be a polymer film consisting of at least one material selected from polyester, polycarbonate, polystylene, polyimide, polyvinylchloride, polyethylene, or polyethyleneterephthalate(PET). The insulating substrate 180 is prepared by cutting the polymer film in a desired size through a cutting process.

Figure 9:
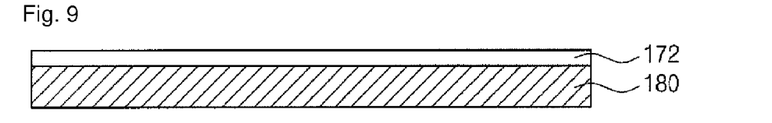

As illustrated in FIG. 9, a first conductive thin film 172 is adhesively applied on the insulating substrate 180 by lamination. The first conductive thin film 172 forms an electrode material, and may be, if not limited to, a copper film or a copper alloy film partly consisting of a copper component such as brass or bronze. It is apparent to those skilled in the art that films of another conductive material may also be used.

Figure 10:
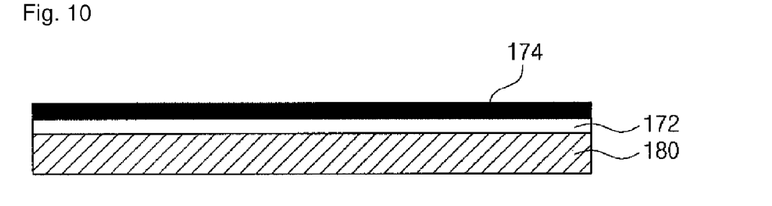

As illustrated in FIG. 10, a photosensitivity dry film 174 for forming electrodes is applied on the insulating substrate 180 on which the first conductive thin film 172 is formed. The photosensitivity dry film 174 is coated on the insulating substrate 180 having the first conductive thin film 172 by lamination. For example, lamination is carried out by rolling coating with a laminating machine at a preheat temperature of about 100 to 120° C. It is apparent to those skilled in the art that the photosensitivity dry film 174 may be coated in the temperature range other than about 100 to 120° C.

Figure 11:
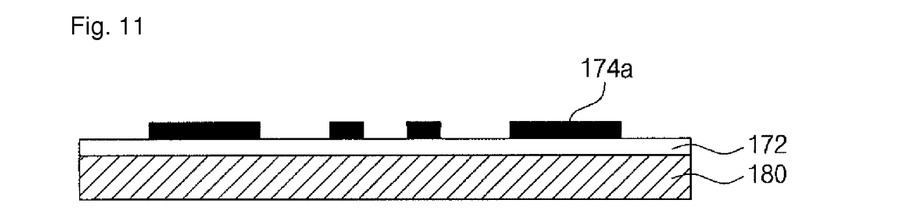

As illustrated in FIG. 11, exposure and development are carried out as a photo process.

For the exposure process, a working film (not shown) (for example, negative film) is aligned on the laminated photosensitivity dry film 174. Under a light energy with a predetermined intensity for a predetermined exposure time, part of the dry film to be electrodes is subjected to reaction from monomer into polymer to reproduce a desired pattern image.

In the subsequent development process, part of the dry film that is not converted to polymer throughout the exposure process, namely, the monomer part of the dry film without light exposure is chemically removed with sodium carbonate ($Na_2CO_3$), leaving a mask pattern 174a for formation electrodes on the photosensitivity dry film 174.

Figure 12:
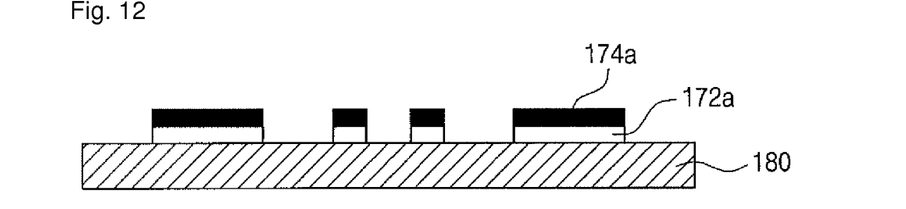

As illustrated in FIG. 12, the etching process is carried out with an etching solution such as an acid-etchant ($CuCl_2$, $FeCl_2$, etc.) solution to remove part of the first conductive thin film 172 on the insulating substrate 180 as covered with the photosensitivity dry film 174, that is, an exposed part of the first conductive thin film 172 other than the electrode pattern. The etching process may include any other etching methods such as dry etching or plasma etching as well as wet etching.

The above-described etching process gives the base of the electrode pattern 172a as shown in FIG. 1. The mast pattern 174a is then removed in a separate process.

Figure 13:
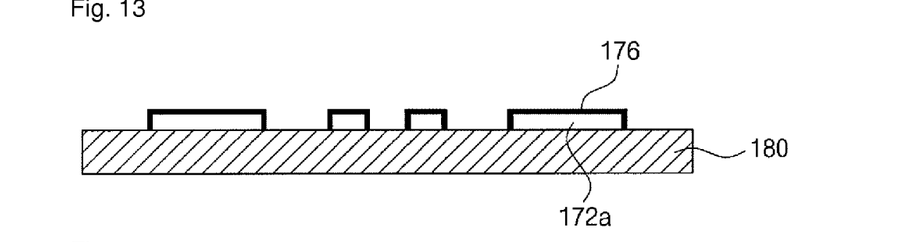

As illustrated in FIG. 13, the plating process is carried out to form a nickel(Ni) thin film 176.

In case of a washing process done after the etching process, the process of forming the nickel(Ni) thin film 176 may follow the washing process.

Figure 14:
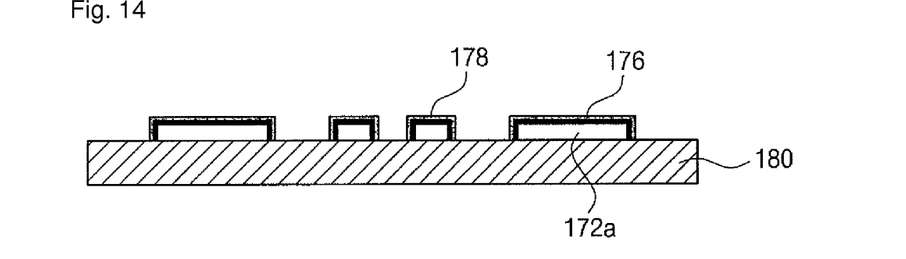

The nickel (Ni) thin film 176 is provided for enhancing adherence and adhesion strength between the electrode pattern 172a and the second conductive thin film 178 in the following process of forming the second conductive thin film 178. The process of plating the nickel thin film 176 may be omitted when there is no need of enhancing adherence and adhesion strength, or when separate meanings is used to enhance adherence and adhesion strength. Nickel(Ni) may be replaced with another material such as chrome(Cr).

As illustrated in FIG. 14, the second conductive thin film 178 is formed on the insulating substrate 180 on which the electrode pattern 172a or the nickel or chrome thin film 176 is provided. Plating gold(Au) or platinum(Pt) is used for the second conductive thin film 178. The measurement through electrochemical biosensor electrodes mostly employs the measurement of current, and the current flows along the surface of the electrodes. In forming the biosensor electrodes, accordingly, thin plating of a novel metal such as gold or platinum on the surface of the electrodes lowers the production cost and remarkably reduces the resistance component to about 0.1Ω.

The nickel or chrome thin film and the second conductive thin film that lie in a part other than the biosensor electrodes may be removed in every step through a separate process, or all removed at a time after formation of the second conductive thin film 178.

Subsequently, the washing and drying process is carried out to eliminate the solution remaining on the surface from the platinum plating process to complete the biosensor electrode structure as shown in FIG. 1, that is, the test strip bottom plate 100.

If not shown in the drawings, the process of forming the test strip middle plate 200 having the structure of FIGS. 2 to 5 follows the formation of the test strip bottom plate 100. The process for forming the test strip top plate 300 having the structure of FIGS. 2 to 5 is then additionally performed to complete the test strip type electrochemical biosensor.

While this invention has been described in connection with the embodiments, it is to be understood to those skilled in the art that the description is not intended to be exhaustive or to limit the scope of the invention. Many modifications and variations are possible in light of the above teaching without departing from the scope of the following claims.

INDUSTRIAL APPLICABILITY

The present invention minimizes the effect of the double layer capacitance, independently applies the sample recognition signal, and accurately detects the sample insert time and velocity irrespective of the viscosity of the sample to be measured. Additionally, the present invention has no problem in regard to a distortion of the measurement signal in taking a measurement of the sample, so the sample measurement can be accomplished more rapidly with high reproducibility.

The invention claimed is:

1. An electrochemical biosensor electrode structure comprising:
   a working electrode and a reference electrode used as electrodes for sample measurement being arranged separately from each other in lengthwise direction of a sample insertion path,
   the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode; and
   at least two sample recognition electrodes used as electrodes for sample recognition being separated from each other and arranged adjacent and parallel to the working electrode and the reference electrode,
   wherein the working electrode and the reference electrode are separated from each other at a first separation distance in a portion corresponding to the sample insertion path,
   the at least two sample recognition electrodes are arranged in parallel and separated from each other at a second separation distance, with ends of each said sample recognition electrode spaced from one another and separately terminating adjacent the protection and recess of the working and reference electrodes, the projection and recess of the working and reference electrodes extending to the ends of each said sample recognition electrode, and
   the first separation distance is greater than the second separation distance.

2. The electrochemical biosensor electrode structure as claimed in claim 1, wherein the at least two sample recognition electrodes are arranged between the working electrode and the reference electrode, the ends of the at least two sample recognition electrodes being adjacent to the end of the sample insertion path.

3. The electrochemical biosensor electrode structure as claimed in claim 2, wherein the at least two sample recognition electrodes recognize a sample in response to a sample recognition signal, the sample recognition signal being applied independent of a sample measurement signal applied to the reference electrode or the working electrode to recognize the sample.

4. The electrochemical biosensor electrode structure as claimed in claim 1, further comprising:
   a strip recognition electrode for sensing the moment that a biosensor having the biosensor electrode is inserted into a measurement device to take a measurement.

5. The electrochemical biosensor electrode structure as claimed in claim 1, wherein the working electrode and the reference electrode are separated from each other at a separation distance of 50 to 120 µm in a portion thereof corresponding to the sample insertion path.

6. A structure for electrochemical biosensor comprising:
   a bottom plate comprising electrodes for sample measurement, and at least two sample recognition electrodes arranged separately from the electrodes for sample measurement on an insulating substrate, the electrodes for sample measurement including a working electrode and a reference electrode,
   the working electrode and the reference electrode being arranged separately from each other in lengthwise direction of a sample insertion path,
   the working electrode and the reference electrode each having at least one projection and at least one recess alternately arranged on a portion thereof corresponding to the sample insertion path, the projection of the working electrode being correspondingly adjacent to the recess of the reference electrode, the recess of the working electrode being correspondingly adjacent to the projection of the reference electrode,
   the at least two sample recognition electrodes being separated from each other and arranged adjacent and parallel to the working electrode and the reference electrode;
   a middle plate having a double-coated adhesive insulating film structure with the sample insertion path formed thereon defined as a notch through an end thereof, the sample insertion path having an end extending to and positioned above tips of the at least two sample recognition electrodes; and
   a top plate having at least two air exhaust through holes each being formed through the insulating substrate and each being positioned above the end of the sample insertion path and respective tips of the at least two sample recognition electrodes in correspondence to the end of the sample insertion path and respective tips of the at least two sample recognition electrodes,
   the at least two air exhaust holes being provided correspondingly to the ends of the at least two sample recognition electrodes to vertically overlap the ends of the at least two sample recognition electrodes,
   wherein the working electrode and the reference electrode are separated from each other at a first separation distance in a portion corresponding to the sample insertion path,
   the at least two sample recognition electrodes are arranged in parallel and separated from each other at a second separation distance, the first separation distance is greater than the second separation distance, and the tips of the at least two sample recognition electrodes spaced from one another and separately terminating working and reference electrodes the projection and recess of the working and reference electrodes extending normally to the tips of each said sample recognition electrode.

7. The structure for electrochemical biosensor as claimed in claim 6, wherein the at least two sample recognition electrodes recognize a sample in response to a sample recognition signal, the sample recognition signal being applied independent of a sample measurement signal applied to the reference electrode or the working electrode to recognize of the sample.

8. The structure for electrochemical biosensor as claimed in claim 6, wherein a first sample recognition electrode as the one of the at least two sample recognition electrodes is provided for applying a sample recognition signal, a second sample recognition electrode as the other one of the at least two sample recognition electrodes being provided for receiving a sample arrival signal.

9. The structure for electrochemical biosensor as claimed in claim 6, wherein the working electrode and the reference electrode are separated from each other at a separation distance of 50 to 120 μm in a portion thereof corresponding to the sample insertion path.

\* \* \* \* \*